United States Patent
Yamaki

(10) Patent No.: US 10,275,905 B2
(45) Date of Patent: Apr. 30, 2019

(54) COLOR INTEGRATION SYSTEM FOR MEDICAL IMAGES AND RECORDING AND COLOR MANAGEMENT APPARATUS FOR MEDICAL IMAGES

(71) Applicant: OLYMPUS CORPORATION, Hachioji-shi, Tokyo (JP)

(72) Inventor: Masahide Yamaki, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/414,297

(22) Filed: Jan. 24, 2017

(65) Prior Publication Data

US 2017/0132811 A1    May 11, 2017

Related U.S. Application Data

(63) Continuation of application No. PCT/JP2015/065296, filed on May 27, 2015.

(30) Foreign Application Priority Data

Aug. 4, 2014 (JP) ................................. 2014-158916

(51) Int. Cl.
  *H04N 1/60* (2006.01)
  *H04N 5/225* (2006.01)
  (Continued)

(52) U.S. Cl.
  CPC .............. *G06T 11/001* (2013.01); *A61B 1/04* (2013.01); *H04N 1/603* (2013.01);
  (Continued)

(58) Field of Classification Search
  CPC combination set(s) only.
  See application file for complete search history.

(56) References Cited

U.S. PATENT DOCUMENTS

| 5,606,432 A | * | 2/1997 | Ohtsuka | H04N 1/6011 358/501 |
| 2002/0131652 A1 | * | 9/2002 | Yoda | G06T 5/00 382/309 |

(Continued)

FOREIGN PATENT DOCUMENTS

| JP | 2004-80648 A | 3/2004 |
| JP | 2007-111326 A | 5/2007 |

(Continued)

OTHER PUBLICATIONS

Sep. 1, 2015 Search Report issued in International Patent Application No. PCT/JP2015/065296.

*Primary Examiner* — Wesner Sajous
(74) *Attorney, Agent, or Firm* — Oliff PLC

(57) ABSTRACT

A color integration system for medical images includes: first and second profile setting sections configured to set first and second profiles, respectively, for color reproduction; a storage section configured to store a plurality of pieces of conversion information for converting the first profile to the second profile; and a control section, wherein if conversion information corresponding to an output environment for using a medical image for a second time is not stored, the control section acquires a profile for color reproduction in the output environment, generates the conversion information based on a profile in the storage section and one or more pieces among the plurality of pieces of conversion information stored in the storage section, and uses the generated conversion information to convert the first profile to the second profile.

9 Claims, 12 Drawing Sheets

(51) Int. Cl.
  *G06T 11/00*     (2006.01)
  *G06F 3/048*     (2013.01)
  *A61B 1/00*      (2006.01)
  *A61B 1/04*      (2006.01)
  *G06F 3/0484*    (2013.01)

(52) U.S. Cl.
  CPC ......... *H04N 1/6005* (2013.01); *H04N 1/6052* (2013.01); *H04N 1/6077* (2013.01); *A61B 1/00009* (2013.01); *G06F 3/04842* (2013.01); *G06F 3/04845* (2013.01); *G06F 3/04847* (2013.01); *G06T 2200/24* (2013.01); *G06T 2210/41* (2013.01); *H04N 5/225* (2013.01); *H04N 2005/2255* (2013.01); *H04N 2201/0079* (2013.01); *H04N 2201/0089* (2013.01); *H04N 2201/0098* (2013.01)

(56) References Cited

U.S. PATENT DOCUMENTS

| | | | | |
|---|---|---|---|---|
| 2002/0154138 | A1* | 10/2002 | Wada | G09G 3/002 345/600 |
| 2003/0117639 | A1* | 6/2003 | Milton | G06K 15/02 358/1.13 |
| 2003/0176768 | A1* | 9/2003 | Gono | A61B 1/0638 600/109 |
| 2005/0254704 | A1* | 11/2005 | Komiya | H04N 5/2256 382/162 |

FOREIGN PATENT DOCUMENTS

JP  2007-336198 A   12/2007
JP  2013-183834 A   9/2013

* cited by examiner

FIG. 3

|    | ESOPHAGUS | STOMACH | DUODENUM | SMALL INTESTINE | LARGE INTESTINE | OTHERS |
|----|-----------|---------|----------|-----------------|-----------------|--------|
| GI | ID=101 | ID=102 | ID=103 | ID=104 | ID=105 | ID=106 |
|    | GALL BLADDER | LARGE INTESTINE | STOMACH/ DUODENUM | ESOPHAGUS | PANCREAS, BILIARY, AND LIVER | HERNIA |
| SP | ID=201 | ID=202 | ID=203 | ID=204 | ID=205 | ID=206 |

FIG. 4

| COLOR TONE ADJUSTMENT | C-R ⌈−14⌋〜⌈14⌋ | CONTRAST | ⌈−14⌋〜⌈14⌋ |
|---|---|---|---|
|  | M-G ⌈−14⌋〜⌈14⌋ | BRIGHTNESS | ⌈−14⌋〜⌈14⌋ |
|  | Y-B ⌈−14⌋〜⌈14⌋ | SHARPNESS | ⌈1⌋〜⌈15⌋ |
| GAMMA | "SOFT" "NORMAL" "HARD" | COLOR DENSITY | ⌈−13⌋〜⌈14⌋ |

FIG. 5

| COLOR TONE | (C-R,M-G,Y-B) | {+4, +1, +8} |
|---|---|---|
| GAMMA | GAMMA VALUE | {×1.2} |
| CONTRAST | CONTRAST VALUE | {−5} |
| BRIGHTNESS | BRIGHTNESS VALUE | {+4} |

FIG. 13

| SCENE ||
|---|---|
| SCENE NUMBER | COEFFICIENT SEQUENCE |
| No. 1 | A{X1, X2, X3···} |
| No. 2 | B{X1, X2, X3···} |
| No. 3 | C{X1, X2, X3···} |
| No. 4 | D{X1, X2, X3···} |
| No. 5 | E{X1, X2, X3···} |
| No. 6 | F{X1, X2, X3···} |
| User | G{Y1, Y2, Y3···} |

COLOR INTEGRATION SYSTEM FOR MEDICAL IMAGES AND RECORDING AND COLOR MANAGEMENT APPARATUS FOR MEDICAL IMAGES

CROSS REFERENCE TO RELATED APPLICATION

This application is a continuation application of PCT/JP2015/065296 filed on May 27, 2015 and claims benefit of Japanese Application No. 2014-158916 filed in Japan on Aug. 4, 2014, the entire contents of which are incorporated herein by this reference.

BACKGROUND OF THE INVENTION

1. Field of the Invention

The present invention relates to a color integration system for medical images and a recording and a color management apparatus for medical images that can obtain optimal color reproducibility in any device.

2. Description of the Related Art

In recent years, medical observation apparatuses, such as an endoscope and a surgical microscope, configured to observe an operated part in medical action, such as surgery, have been widely used. For example, an endoscope is inserted into a body cavity, such as an abdominal cavity and a thoracic cavity, from a small fistula opened on a body surface of a patient, and an organ in the body cavity is treated under endoscopic observation. Such endoscopic surgery is also frequently conducted. The medical observation apparatus includes an image pickup device, and the image pickup device can pick up an image (medical image) inside of the body cavity of the patient. The medical image obtained by picking up the image can be outputted to a monitor or recorded, and the image can be shared among people involved in the surgery, such as a surgeon, an assistant, and a nurse.

Endoscope images used for inspection or treatment during surgery are used for a conference presentation or a case report after the surgery in some cases. One endoscope image is displayed on a plurality of monitors during surgery and is displayed and printed by various monitors, printers, projectors, and the like after the surgery.

In this case, if, for example, a display color of an observation monitor during the inspection or the treatment and an ink display color at submission of the report are different, the surgeon may not be able to properly judge the observation result. Therefore, the surgeon needs to adjust the display color or the print color in each device, and this is very cumbersome.

Note that Japanese Patent Application Laid-Open Publication No. 2007-111326 discloses an endoscope system in which image processing for monitor display and image processing for printer printing are applied to an image from an endoscope to obtain favorable image quality in both of the image for display and the image for printing. Japanese Patent Application Laid-Open Publication No. 2007-336198 discloses a technique in an apparatus configured to convert color with reference to a profile defining a correspondence between colorimetric values and ink amount data, wherein different profiles are created according to the usage and conditions.

In a latest consumer technology, a color profile, such as Exif and ICC profiles, is provided from a manufacturer for each display and each printer, and the color profiles can be transmitted between respective systems to bring the display colors into line with each other regardless of the printer.

SUMMARY OF THE INVENTION

An aspect of the present invention provides a color integration system for medical images including: a first profile setting section configured to set a first profile that is setting information for color reproduction in a plurality of first output environments for outputting a medical image; a second profile setting section configured to set a second profile for color reproduction in a plurality of second output environments for using the medical image for a second time; a storage section configured to store a plurality of pieces of conversion information for conversion to the second profile set by the second profile setting section based on a setting result of the first profile setting section; a control section configured to use the conversion information stored in the storage section to convert the first profile to the second profile; and a data generation section configured to output the second profile in association with the medical image, wherein if conversion information corresponding to an output environment for using the medical image for a second time is not stored in the storage section, the control section acquires a profile for color reproduction in the output environment, generates conversion information for converting the first profile to the second profile based on the acquired profile and one or more pieces among the plurality of pieces of conversion information stored in the storage section, and uses the generated conversion information to convert the first profile to the second profile.

An aspect of the present invention provides a recording and color management apparatus for medical images including: an acquisition section capable of setting a first profile that is setting information for color reproduction related to a medical image and configured to acquire the first profile from a display apparatus capable of outputting the first profile; a storage section configured to store a plurality of pieces of conversion information for converting the first profile to a second profile for color reproduction in one of a plurality of output environments for using the medical image for a second time; a control section configured to use the plurality of pieces of conversion information stored in the storage section to convert the first profile acquired by the acquisition section to the second profile; and a data generation section configured to output the second profile converted by the control section in association with the medical image.

BRIEF DESCRIPTION OF THE DRAWINGS

FIG. 3 is a chart for describing IDs for selecting one of a plurality of preset profiles;

FIG. 4 is an explanatory view showing an example of a base profile;

FIG. 5 is an explanatory view showing an example of conversion information from the base profile to a secondary use profile;

FIG. 13 is an explanatory view showing coefficient sequences of conversion information corresponding to scene numbers.

DETAILED DESCRIPTION OF THE PREFERRED EMBODIMENT(S)

Hereinafter, embodiments of the present invention will be described in detail with reference to the drawings.

(First Embodiment)

Figure 1:
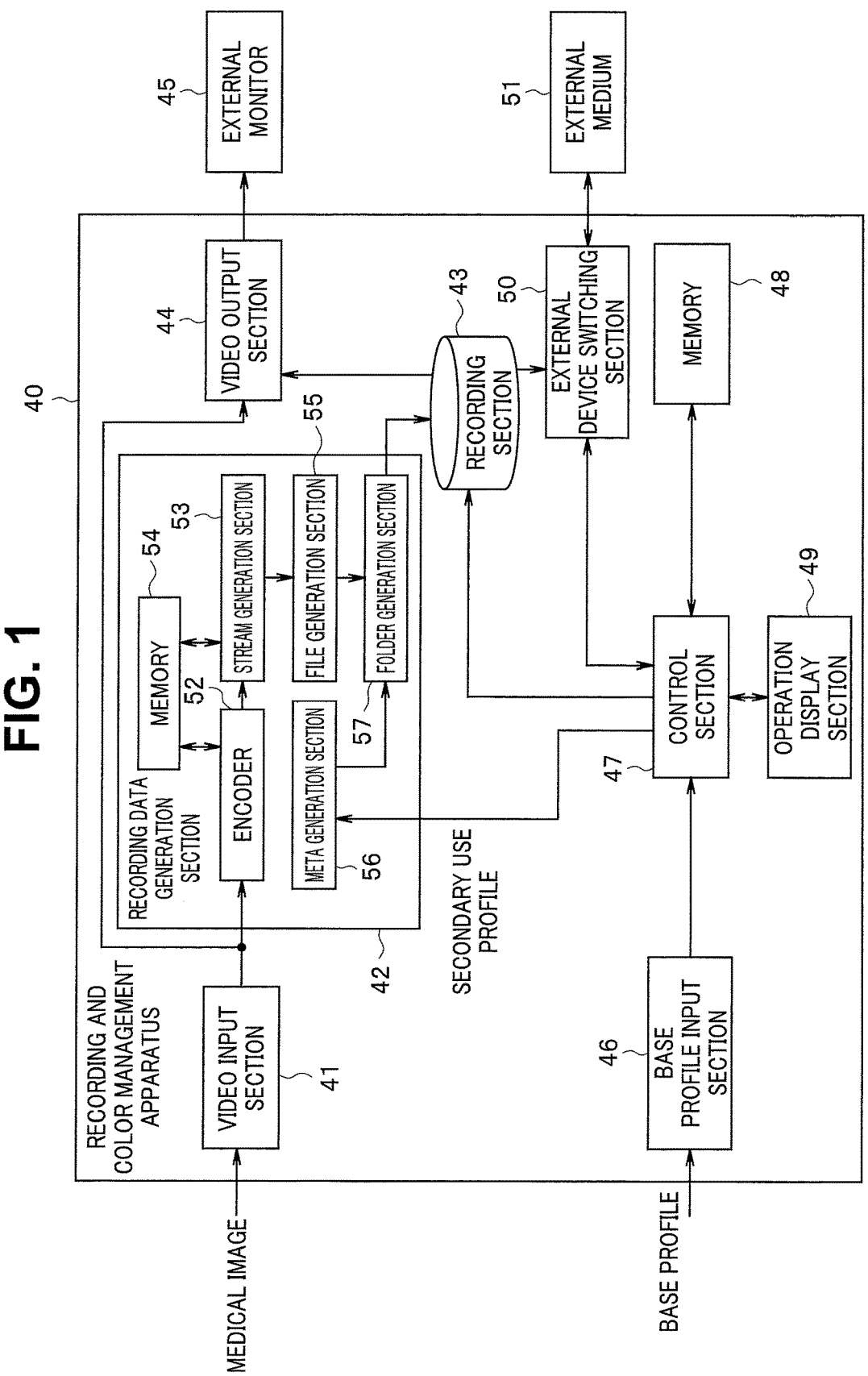
FIG. 1 is a block diagram showing a color integration system of a medical image according to a first embodiment of the present invention.
Figure 2:
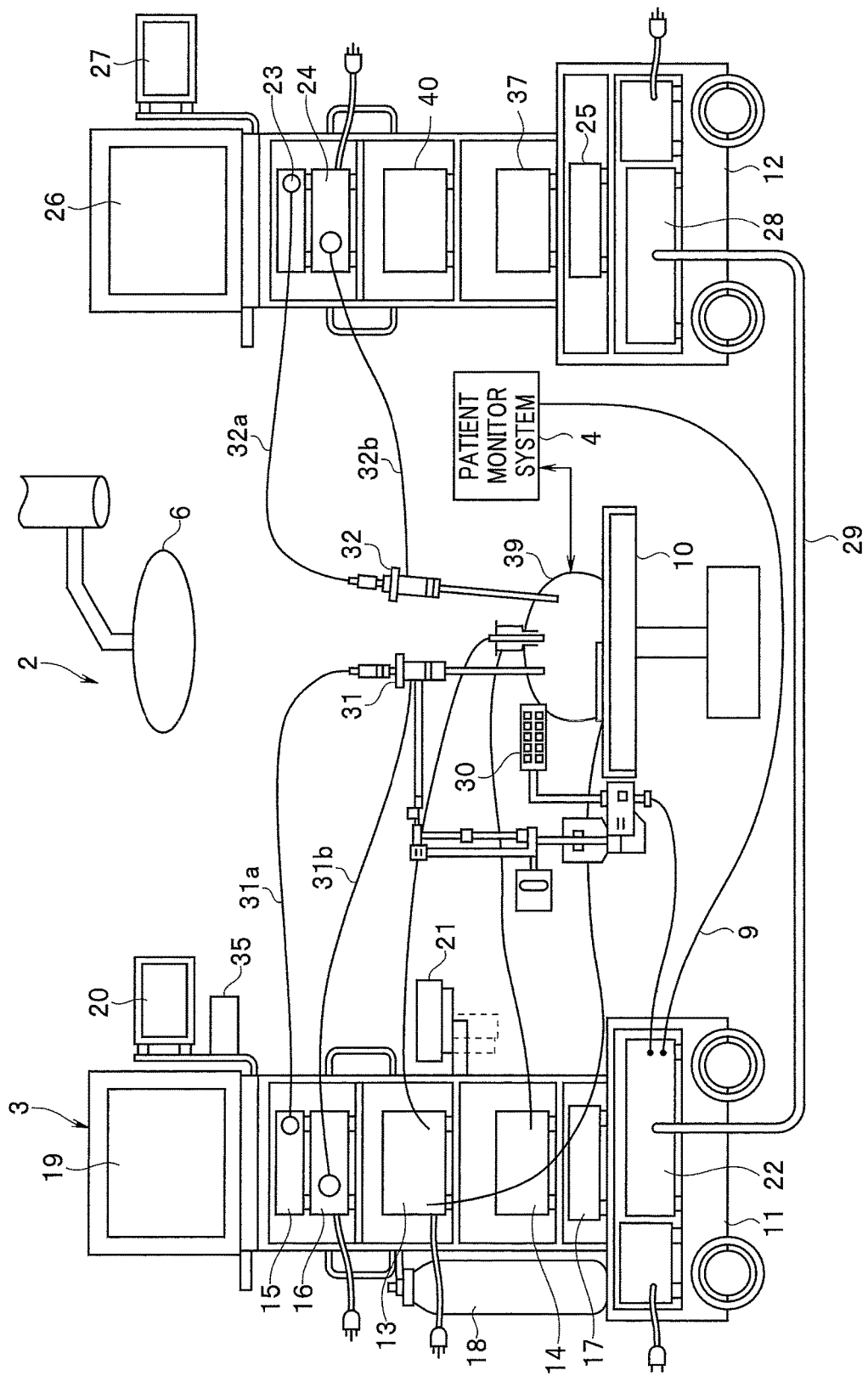
FIG. 2 is an external view showing an example of a medical system for creating the medical image.

FIG. 1 is a block diagram showing a color integration system of a medical image according to a first embodiment of the present invention. FIG. 2 is an external view showing an example of a medical system for creating a medical image. The present embodiment enables to refer to conversion information (conversion table) of a profile (hereinafter, called base profile) based on setting information for determining a color of the medical image displayed on a monitor during surgery and a profile of a device at a place of using the medical image to thereby obtain a profile (hereinafter, called secondary use profile) to be used in the device at the place of using the medical image. The present embodiment enables to output the secondary use profile in association with the medical image.

Note that in the present specification, the profile is setting information for color reproduction in a predetermined output environment of the image. For example, the profile denotes setting information for obtaining appropriate color reproducibility in a corresponding device, and an original profile can be usually set in each device. Examples of the information included in the profile include color temperature, gamma, luminance, contrast, chroma, color balance, gray balance, brightness, and various other setting information.

Although the present embodiment describes an example in which a profile of a monitor used for observation during the surgery is used as the base profile, profiles of other devices may be used as the base profile, and profiles of fictional devices may also be used.

First, an overall configuration of a medical system 3 disposed in an operating room 2 will be described with reference to FIG. 2.

As shown in FIG. 2, a patient bed 10 on which a patient 39 lies down, a shadowless lamp 6, and the medical system 3 are disposed in the operating room 2. The medical system 3 includes a first cart 11 and a second cart 12.

Examples of medical devices mounted on the first cart 11 include apparatuses, such as an electric scalpel apparatus 13, a pneumoperitoneum apparatus 14, an endoscope camera apparatus 15, a light source apparatus 16, and a video recorder 17, and a gas cylinder 18 filled with carbon dioxide. The endoscope camera apparatus 15 is connected to a first endoscope 31 through a camera cable 31a.

The light source apparatus 16 is connected to the first endoscope 31 through a light guide cable 31b. A display apparatus 19, a first central display panel 20, an operation panel 21, and the like are also mounted on the first cart 11. The display apparatus 19 is, for example, a TV monitor configured to display endoscope images.

The central display panel 20 is display means capable of selectively displaying any data during the surgery. The operation panel 21 is configured by a display section, such as a liquid crystal display, and a touch sensor integrally provided on the display section, for example. The operation panel 21 is a central operation apparatus operated by a nurse or the like in a non-sterile area.

A system controller 22 that is a central control apparatus is further mounted on the first cart 11. The shadowless lamp 6, the electric scalpel apparatus 13, the pneumoperitoneum apparatus 14, the endoscope camera apparatus 15, the light source apparatus 16, and the video recorder 17 are connected to the system controller 22 through communication lines not shown. A headset microphone not shown can also be connected to the system controller 22, and the system controller 22 can recognize voice inputted from the microphone to control each device based on the voice of a surgeon.

The first cart 11 is also provided with an RFID (radio frequency identification) terminal 35 capable of wirelessly reading and writing individual ID info/illation of things based on ID tags embedded in the first endoscope 31, a treatment instrument of the electric scalpel apparatus 13, and the like.

On the other hand, an endoscope camera apparatus 23, a light source apparatus 24, an image processing apparatus 25, a display apparatus 26, a second central display panel 27, a printer 37, and a recording and color management apparatus 40 are mounted on the second cart 12. The endoscope camera apparatus 23 is connected to a second endoscope 32 through a camera cable 32a. The light source apparatus 24 is connected to the second endoscope 32 through a light guide cable 32b.

The display apparatus 26 displays endoscope images and the like captured by the endoscope camera apparatus 23. The second central display panel 27 can selectively display any data during the surgery.

The endoscope camera apparatus 23, the light source apparatus 24, the image processing apparatus 25, the printer 37, and the recording and color management apparatus 40 are connected to an intermediate unit 28 mounted on the second cart 12 through communication lines not shown. The intermediate unit 28 is connected to the system controller 22 mounted on the first cart 11 through an intermediate cable 29.

In this way, the system controller 22 can comprehensively control the camera apparatus 23, the light source apparatus 24, the image processing apparatus 25, the printer 37, and the recording and color management apparatus 40 mounted on the second cart 12 as well as the electric scalpel apparatus 13, the pneumoperitoneum apparatus 14, the camera apparatus 15, the light source apparatus 16, and the video recorder 17 mounted on the first cart 11. Therefore, when there is communication between the system controller 22 and the apparatuses, the system controller 22 can display a setting screen of setting states of connected apparatuses, operation switches, and the like on the liquid crystal display of the operation panel 21. The system controller 22 also allows inputting operation, such as changing a set value, when a desired operation switched is touched to operate a touch sensor of a predetermined area.

A remote controller 30 is a second central operation apparatus operated by an operating surgeon or the like in a sterile area. The remote controller 30 can operate other communicating apparatuses through the system controller 22.

The system controller 22 is connected to a patient monitor system 4 through a cable 9. The patient monitor system 4 can analyze biological information and display the analysis result on a required display apparatus.

An infrared communication port (not shown) that is communication means is also attached to the system controller 22. The infrared communication port is provided on a position, such as near the display apparatus 19, where infrared can be easily applied, and the infrared communication port and the system controller 22 are connected by a cable.

In FIG. 1, a medical image obtained by an endoscope processor or the like is inputted to a video input section 41 of the recording and color management apparatus 40. For example, an image from the image processing apparatus 25 of FIG. 2 is inputted as a medical image to the recording and color management apparatus 40. The video input section 41 outputs the inputted medical image to a recording data generation section 42 and a video output section 44.

The video output section 44 can output the inputted medical image to an external monitor 45 as it is. The external monitor 45 corresponds to, for example, the display apparatuses 19 and 26 of FIG. 2 and displays the inputted medical image. In this case, the surgeon can adjust the external monitor 45 to display the medical image in a desired color.

For example, a profile based on the setting of color of the external monitor 45 is used as a base profile. The external monitor 45 has a function of generating a profile based on the setting by the surgeon and can output the generated profile. Note that when the surgeon does not perform the setting, an initial set value of the external monitor 45 is outputted as the base profile. In the present embodiment, the base profile is provided to a base profile input section 46 of the recording and color management apparatus 40. Note that if the external monitor 45 and the base profile input section 46 have similar communication functions, the base profile from the external monitor 45 can be provided to the base profile input section 46 through communication. Another recording medium may be used to provide the base profile from the external monitor 45 to the base profile input section 46. When the system controller 22 of FIG. 2 can control the external monitor 45, the system controller 22 may generate a profile based on the control of the external monitor 45 to provide the generated profile as the base profile to the base profile input section 46.

The base profile input section 46 provides the inputted base profile to a control section 47. In the present embodiment, conversion information (conversion table) for converting the base profile to a secondary use profile is stored in a memory 48. The control section 47 is configured by a processor or the like, and the control section 47 can read a conversion table from the memory 48 according to a device that uses the medical image for a second time and can convert the base profile to the secondary use profile based on the read conversion table. Note that when conversion coefficients are stored as conversion information in the memory 48, it is apparent that the control section 47 may obtain the secondary use profile through calculation of respective pieces of the setting information of the base profile and the conversion coefficients. Note that the conversion from the base profile to the secondary use profile will be described later.

A plurality of profiles may be prepared in advance as base profiles in the present embodiment, and the base profile may be set by selecting one profile through selection operation by a user, such as selection according to a case or a scene. An operation display section 49 can receive such user operation and can output an operation signal based on the user operation to the control section 47. For example, a plurality of profiles may be preset in the memory 48, and the control section 47 may be caused to select one profile from the memory 48 according to the user operation of the operation display section 49 to read the profile as the base profile.

The device that uses the medical image for a second time can also be designated by the user operation of the operation display section 49. The control section 47 creates a secondary use profile by reading a conversion table corresponding to the device designated based on the user operation of the operation display section 49. Note that the control section 47 can display a menu display or the like for receiving the user operation on a display screen of the operation display section 49.

The control section 47 outputs the secondary use profile generated from the base profile to the recording data generation section 42. The recording data generation section 42 is controlled by the control section 47 to encode the medical image inputted from the video input section 41 into a video signal in a predetermined image format suitable for recording, and the recording data generation section 42 provides and records the video signal in a recording section 43.

The recording data generation section 42 includes an encoder 52. The encoder 52 converts the inputted medical image to a video signal in a predetermined format, such as a video signal in an MPEG2 format or an MPEG-4AVC/H.264 format, while storing the medical image in a memory 54 and outputs the video signal to a stream generation section 53. The stream generation section 53 converts the inputted video signal to a bit stream in a predetermined format and outputs the bit stream to a file generation section 55. The file generation section 55 generates a movie file based on the inputted bit stream and provides the movie file to a folder generation section 57. The folder generation section 57 generates an inspection folder for storing the movie file generated by the file generation section 55. The movie file and the inspection folder are supplied to the recording section 43. The recording section 43 can be, for example, a built-in HDD (hard disk apparatus), and the recording section 43 is controlled by the control section 47 to record the output of the recording data generation section 42.

In the present embodiment, the control section 47 provides the secondary use profile corresponding to the device at the place of use to the recording data generation section 42, and the recording data generation section 42 can record the secondary use profile in association with the medical image to be recorded. For example, the secondary use profile from the control section 47 is provided to a meta generation section 56 of the recording data generation section 42. The meta generation section 56 converts the secondary use profile to metadata corresponding to the format of the medical image and provides the metadata to the folder generation section 57 to record the metadata in association with the corresponding medical image.

That is, the profile based on the color setting of the external monitor 45 for displaying, in a desired color, the medical image observed during the surgery is converted to the secondary use profile corresponding to the device that uses the medical image for a second time, and the secondary use profile is recorded in the recording section 43 in association with the medical image.

An output destination of the recording section 43 is controlled by the control section 47, and the recording section 43 is configured to output the recorded medical image to the video output section 44 and an external device switching section 50. When a compressed medical image is inputted from the recording section 43, the video output section 44 can decode the inputted medical image and then output the medical image to the external monitor 45.

The external device switching section 50 is controlled by the control section 47, and the external device switching section 50 can output and save the recording data of the recording section 43 in a predetermined external medium 51. Examples of a predetermined recording medium include a semiconductor memory, a USB device, an optical medium, a personal computer, a server, and various other recording media. The medical image recorded in the external medium 51 is recorded in association with the secondary use profile.

When the medical image recorded in the external medium 51 is used by the device that uses the medical image for a second time, the device reads the secondary use profile associated with the medical image and sets the color. The secondary use profile is created according to the base profile based on the setting of the external monitor 45 set by the surgeon to display the medical image in a preferred color. Cumbersome setting is not necessary in the device that uses the medical image for a second time, and the medical image can be displayed or printed in the same color as the color in the external monitor 45.

(Conversion from Base Profile to Secondary Use Profile)

FIG. 3 is a chart for describing IDs for selecting one of a plurality of preset profiles. The example in FIG. 3 is for generation of a recommended color for each field and case. The example in FIG. 3 shows that IDs for diagnosis or the like of each of esophagus, stomach, duodenum, small intestine, large intestine, and etc. of a digestive system (GI) are set to 101 to 106 and shows that IDs for diagnosis or the like of each of gall bladder, large intestine, stomach/duodenum, esophagus, pancreas, biliary tract, and liver, and hernia of a surgical system (SP) are set to 201 to 206. Note that recommended set values may be provided by allocating IDs not only for the field and the case (region), but also for each facility environment.

FIG. 4 is an explanatory view showing an example of the base profile. Note that although ranges of possible values in respective setting items are shown in FIG. 4, values based on the setting by the user or the initial setting of the device among the possible values are actually set. For example, FIG. 4 can be a base profile read from the memory 48 after designation of one of the preset profiles by the user based on an ID or the like or can be a profile generated based on the color setting of the external monitor 45 or the like and inputted to the base profile input section 46.

In the example of FIG. 4, the base profile includes setting items of color adjustment, gamma, contrast, brightness, sharpness, and color density. Note that values of C-R (cyan-red), M-G (magenta-green), and Y-B (yellow-blue) are set for the color adjustment, and values of soft, normal, and hard are set for the gamma.

FIG. 5 is an explanatory view showing an example of conversion information from the base profile to the secondary use profile. In the example shown in FIG. 5, a Windows (registered trademark) personal computer is adopted as the device that uses the medical image for a second time. The example in FIG. 5 shows that for the color tone, +4, +1, and +8 are added to the values (C-R, M-G, and Y-B) of the color tone of the base profile, respectively, to obtain values of the color tone of the secondary use profile. Similarly, for the gamma, the value of the gamma (gamma value) of the base profile is multiplied by 1.2 to obtain a value of the gamma of the secondary use profile. Similarly, for the contrast, −5 is added to the value of the contrast (contrast value) of the base profile to obtain a contrast value of the secondary use profile. Similarly, for the brightness, +4 is added to the value of the brightness (brightness value) of the base profile to obtain a value of the brightness of the secondary use profile.

Now, for the base profile read from the memory 48 based on the selection operation by the user or the base profile inputted from the base profile input section 46, it is assumed that the values (C-R, M-G, and Y-B) of the color tone are impixel-11, the value of the gamma is impixel-12, the value of the contrast is impixel-13, and the value of the brightness is impixel-14. In this case, the control section 47 sets {impixel-11}+{+4, +1, +8} as a value impixel-21 of the color tone of the secondary use profile, sets {impixel-12}×{1.2} as a value impixel-22 of the gamma of the secondary use profile, sets {impixel-13}+{−5} as a value impixel-23 of the contrast of the secondary use profile, and sets {impixel-14}+{+4} as a value impixel-24 of the brightness of the secondary use profile. The control section 47 outputs the secondary use profile obtained in this way to the recording data generation section 42.

Note that it is apparent that the control section 47 may use a conversion table based on the conversion information of FIG. 5 to generate the secondary use profile from the base profile.

Although the secondary use profile is recorded in association with the medical image in the description of the present embodiment, the secondary use profile generated based on the base profile may be used without recording the secondary use profile.

Figure 6:
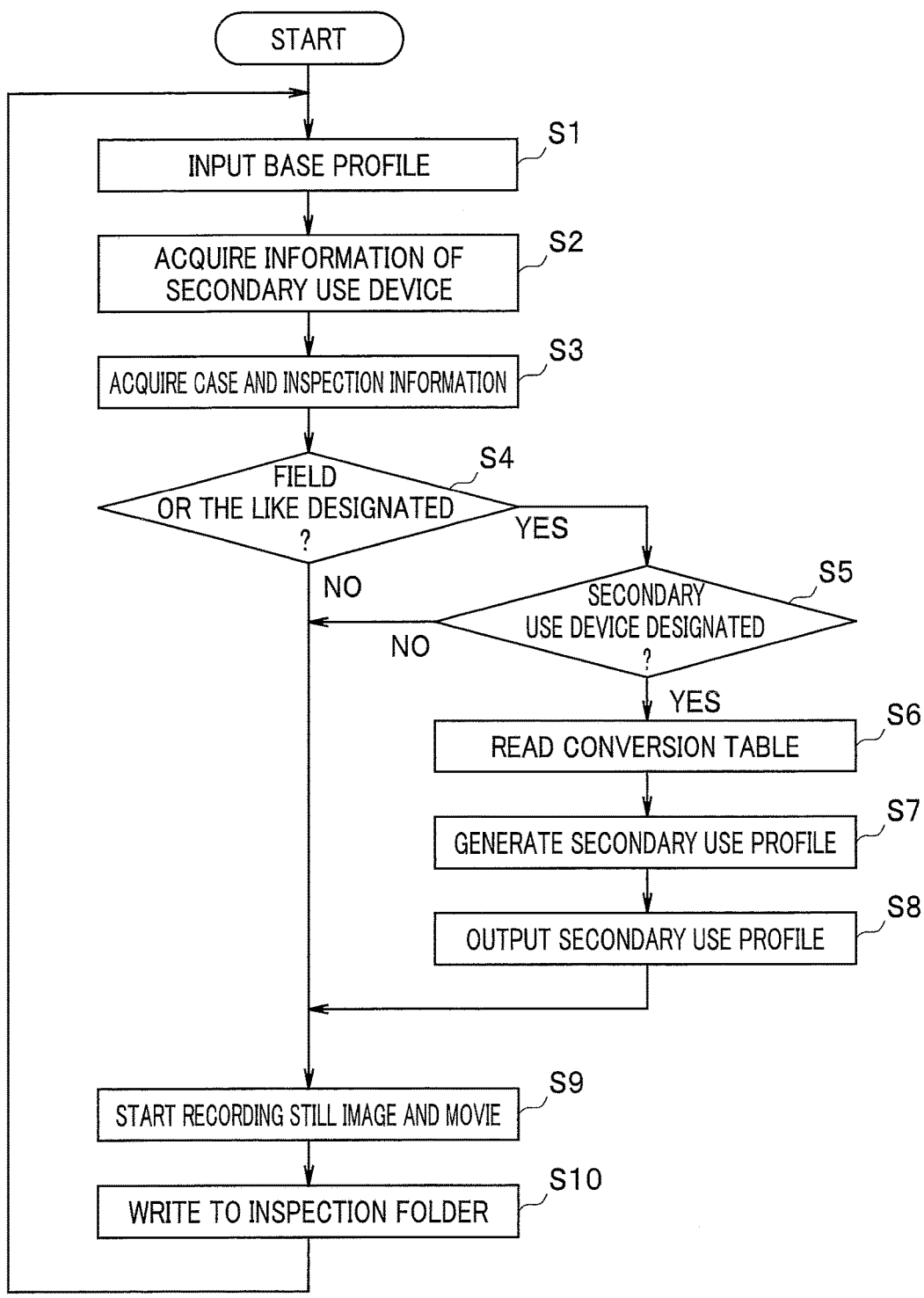
FIG. 6 is a flowchart for describing operation of the first embodiment.
Figure 7:
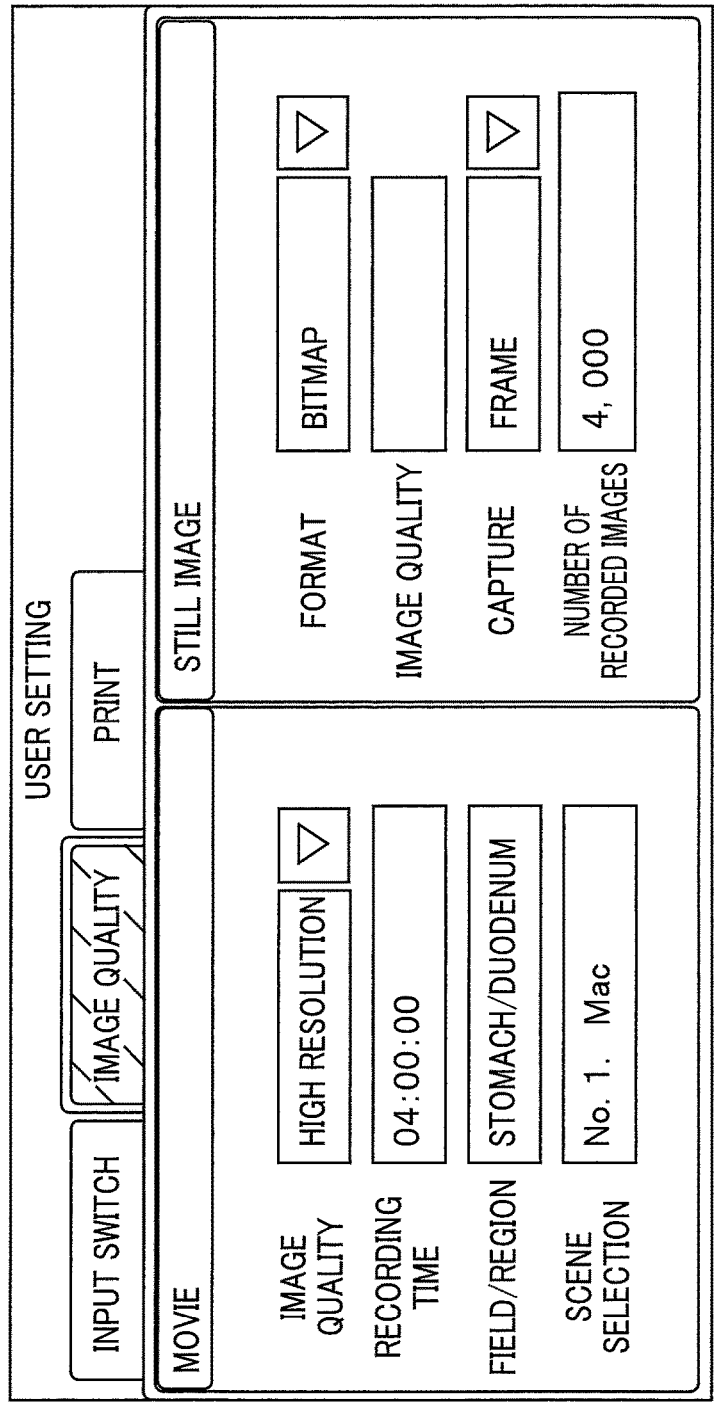
FIG. 7 is an explanatory view showing an example of a setting screen displayed on an operation display section 49.

Next, operation of the embodiment configured in this way will be described with reference to FIGS. 6 and 7. FIG. 6 is a flowchart for describing operation of the first embodiment. FIG. 7 is an explanatory view showing an example of a setting screen displayed on the operation display section 49.

In the present embodiment, the user designates the device that uses the medical image for a second time. The control section 47 displays, for example, a GUI display shown in FIG. 7 on the display screen of the operation display section 49 and receives operation by the user. FIG. 7 shows a user setting screen related to image quality, and the user can set the image quality, recording time, field/region, and the scene selection. In the example of FIG. 7, a scene No. (number) is provided to each scene (output environment) of using the device that uses the medical image for a second time, and the user selects the scene No. to designate the device that uses the medical image for a second time, which is an output environment. Examples of the scene of the secondary use include:

No. 1, use Mac (registered trademark) (OS) PC to view the medical image, Windows (registered trademark) Media Player/Quick Time/dedicated viewer;

No. 2, use Windows (registered trademark) (OS) PC to view the medical image, Quick Time;

No. 3, use a projector to view the medical image;

No. 4, use a commercial monitor to view the medical image;

No. 5, use a consumer monitor to view the medical image;

No. 6, use a video printer to print the medical image; and

No. 7, use a USB printer to print the medical image.

The example of FIG. 7 shows that the user has selected a Mac personal computer as the device that uses the medical image for a second time.

The example of FIG. 7 also shows that stomach/duodenum is selected for the field/region. When the field/region is designated, the control section 47 may use the profile preset in the memory 48 as the base profile, instead of the input from the base profile input section 46. That is, in the example of FIG. 7, the control section 47 uses, as the base profile, the profile registered in advance in the memory 48 for the recommended color of the medical image of stomach/duodenum.

In step S1 of FIG. 6, the control section 47 acquires the base profile from a device such as the external monitor 45. Note that step S1 may be skipped when the user performs operation of designating preset values of the base profile. Next, the control section 47 acquires the information of the device that uses the medical image for a second time based on the user operation (step S2). Next, the control section 47 acquires case and inspection information of the patient that is a subject of the medical image (step S3). Note that step S3 is for recording the medical image in association with the patient. The information may be acquired based on the user operation for the operation display section 49, or the information may be acquired from the system controller 22 of FIG. 2 (not shown).

Next, the control section 47 acquires the information of the field and the case (region) corresponding to the medical image to be recorded in order to acquire the base profile (step S4). Note that step S4 is obtained by the setting of the field/region of FIG. 7, and if the information of the base profile is already acquired in step S1, the acquisition of the profile based on the field and the like can be skipped. The control section 47 can acquire the information of the base profile in step S1 or step S4.

In step S5, the control section 47 judges whether the information of the secondary use scene is inputted. The information is obtained by the scene selection of FIG. 7 in step S2. If the user has not performed the input operation of the information or if the base profile is not acquired in steps S1 and S4, the process shifts to step S9 to start recording a still image and a movie. That is, the control section 47 in this case controls the recording data generation section 42 to record only the medical image in the recording section 43 without associating the secondary use profile with the medial image.

If the control section 47 judges that the secondary use scene is designated in step S5, the control section 47 reads the conversion table corresponding to the designated secondary use scene, that is, the device that uses the medical image for a second time, from the memory 48 (step S6). The control section 47 generates the secondary use profile based on the acquired base profile and the conversion table (step S7).

The control section 47 outputs the generated secondary use profile to the recording data generation section 42 (step S8). In this case, the control section 47 may output meta-information associating the inspection information and the secondary use profile to the recording data generation section 42. In this way, the recording data generation section 42 records the secondary use profile in the recording section 43 in association with the medical image in this case (step S9). The secondary use profile and the inspection information may be recorded in association with the medical image. When the recording is finished, the recording data generation section 42 writes a still image and a movie including the secondary use profile to a predetermined inspection folder (step S10).

To use the medical image in the device that uses the medical image for a second time, the control section 47 controls the external device switching section 50 to provide the medical image that is a still image and a movie including the secondary use profile to the external device switching section 50 to record the medical image in the external medium 51. Note that the external medium 51 may be not only a portable recording medium, but also a recording medium built in a computer or a server. For example, the external medium 51 may be a built-in recording medium of the device that uses the medical image for a second time.

Figure 8:
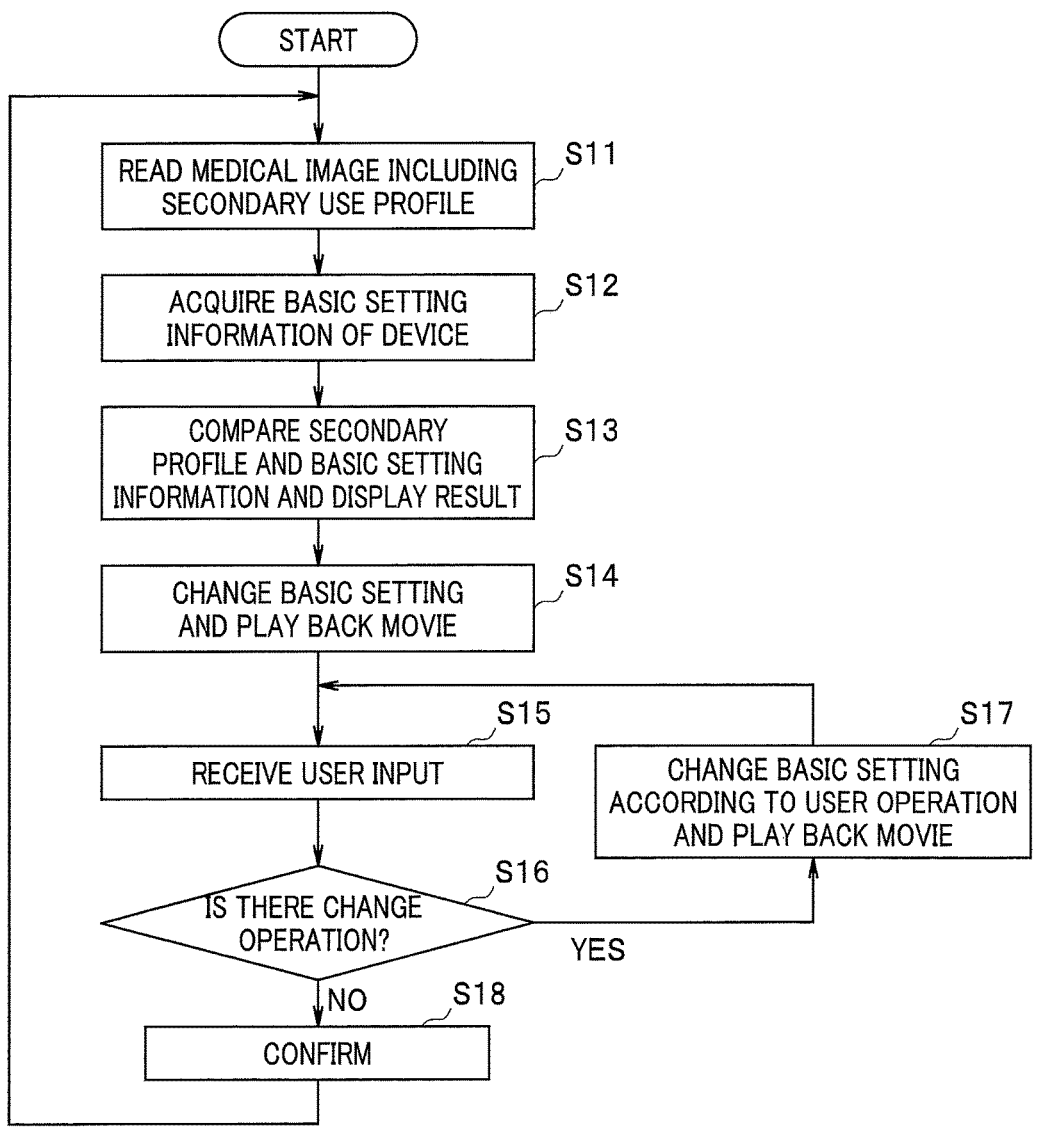
FIG. 8 is a flowchart showing a process in a device that uses the medical image for a second time.
Figure 9:
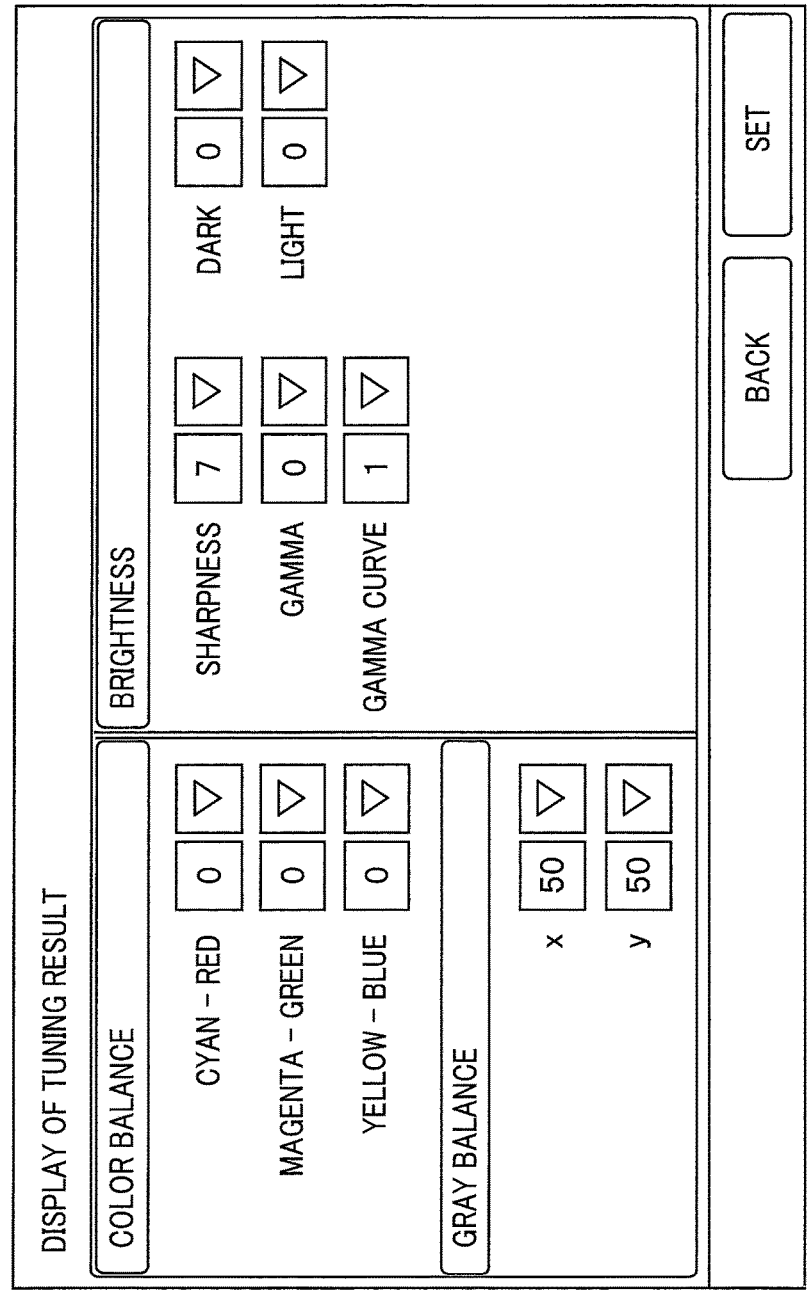
FIG. 9 is an explanatory view showing an example of an adjustment screen of color setting in the device that uses the medical image for a second time.

Next, a process when the device that uses the medical image for a second time uses the medical image including the secondary use profile recorded in this way will be described. FIG. 8 is a flowchart showing a process in the device that uses the medical image for a second time. FIG. 9 is an explanatory view showing an example of an adjustment screen of the color setting in the device that uses the medical image for a second time.

Now, it is assumed that a Mac personal computer designated by the user in the scene selection of FIG. 7 is used as the device that uses the medical image for a second time. FIG. 8 shows a process of a viewing program adopted when the Mac personal computer displays the medical image recorded in the external medium 51. First, the medical image including the secondary use profile is read in step S11. Next, the basic setting information related to the display of the device is acquired (step S12). Next, the secondary use profile and the basic setting information are compared, and an adjustment result is displayed (step S13).

FIG. 9 shows the display and shows that the setting items include color balance, gray balance, and brightness. In the example of FIG. 9, setting values of cyan-red, magenta-green, and yellow-blue can be designated for the color balance, and x and y parameters can be designated for the gray balance. Setting values of sharpness, gamma, gamma curve, dark, and light can be designated for the brightness. The user operates a set button to confirm each of the set values.

Next, the basic set values are changed based on the secondary use profile, and then the changed set values are used to play back the movie of the medical image on a display screen not shown (step S14). In this state, a user input is received (step S15).

The medical image displayed on the display screen is displayed in a color based on the set values according to the secondary use profile. The secondary use profile corresponds to, for example, the base profile obtained when the surgeon changes the setting of the monitor during the surgery, and the secondary use profile corresponds to the set values for displaying the medical image in a color preferred by the surgeon. Therefore, it is likely that the medical image displayed on the display screen is in a color preferred by the surgeon. However, the surgeon can further correct the color of the medical image displayed on the display screen in consideration of, for example, the difference between the environment of the operating room and the environment of the installation location of the device that uses the medical image for a second time.

In this case, the display of FIG. 9 is displayed again, and the set value of each item is designated through, for example, a pull-down menu. When there is setting change operation by the user, the process shifts from step S16 to step S17. The base setting is changed according to the user operation, and then the movie of the medical image is played back. When the user operates the set button without changing the setting, the setting is confirmed (step S1), and the medical image is played back according to the setting at the time.

By the way, although the flow of FIG. 8 illustrates an example in which the user further adjusts the color tone based on the secondary use profile in the device that uses the medical image for a second time, the profile of the adjustment result can also be outputted to use the adjusted profile as the base profile. A flow similar to the flow of FIG. 8 can also be executed by the control section 47 to modify the secondary use profile generated based on the base profile and the conversion information according to the color adjustment by the user, and the modified secondary use profile can be supplied to the recording data generation section 42.

Furthermore, although the surgeon sets the monitor or the like for observing the medical image during the surgery to acquire the base profile in the example illustrated in the description, an optimal color adjustment can be performed in another device, such as a personal computer usually used by the surgeon, and the profile based on the adjustment result can be used as the base profile.

Figure 10:
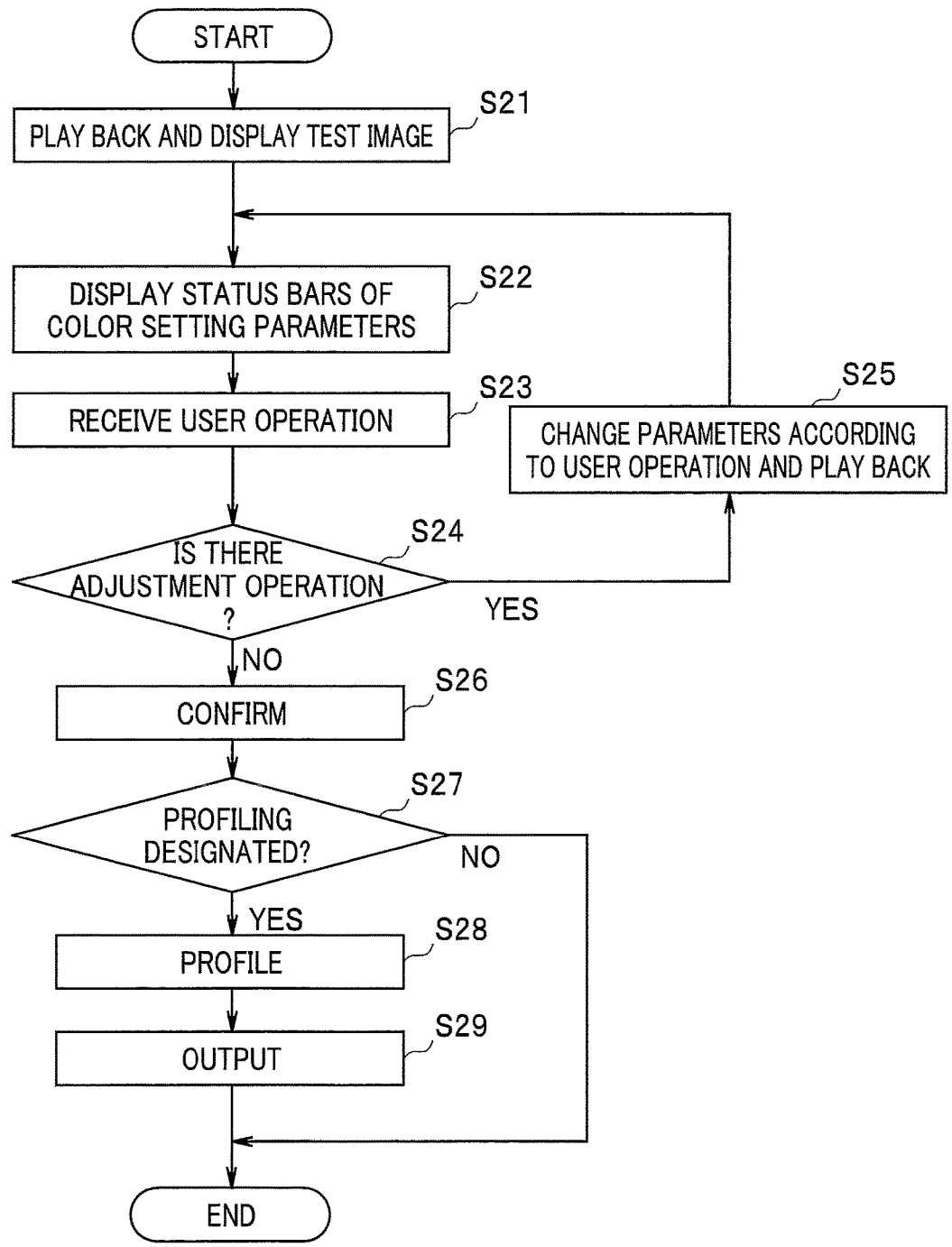
FIG. 10 is a flowchart for describing color adjustment and profiling.
Figure 11A:
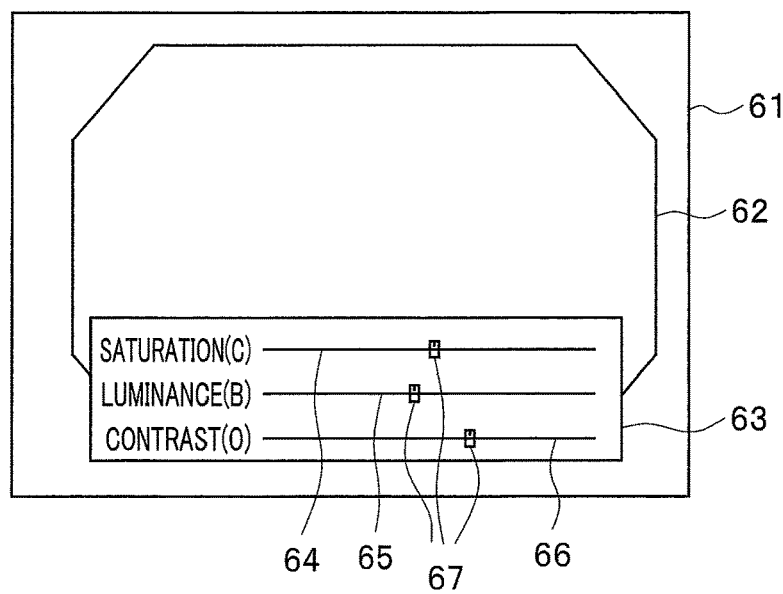
FIG. 11A is an explanatory view showing an example of image display associated with the adjustment.
Figure 11B:
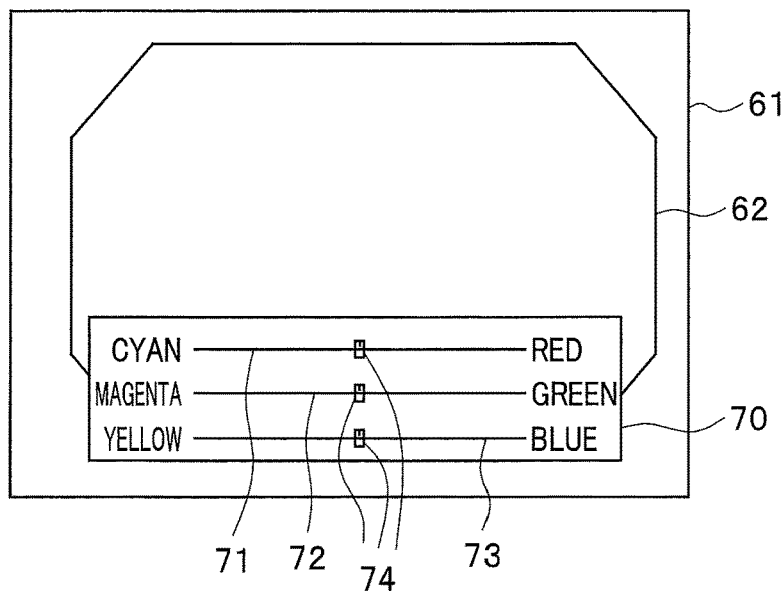
FIG. 11B is an explanatory view showing an example of image display associated with the adjustment.

FIG. 10 is a flowchart for describing the color adjustment and profiling. The flow of FIG. 10 shows a procedure of a program executed by a personal computer, for example. FIGS. 11A and 11B are explanatory views showing examples of image display associated with the adjustment.

In step S21, a predetermined test image is played back and displayed based on the initial values of the color setting. Status bars of color setting parameters are displayed on the test image (step S22). FIGS. 11A and 11B show the display. In the example of display in FIG. 11A, a display area 62 of the test image is provided on a display screen 61, and the test image is displayed in the display area 62 (not shown). A status bar display 63 is displayed below the display area 62. The status bar display 63 includes bar displays 64 to 66 indicating ranges of set values of saturation (C), luminance (B), and contrast (0), respectively. Slide displays 67 indicating the set values of the displayed test image are displayed on the bar displays 64 to 66, respectively.

In the example of display in FIG. 11B, a status bar display 70 is displayed below the display area 62. The status bar display 70 includes bar displays 71 to 73 indicating ranges of set values of cyan-red, magenta-green, and yellow-blue, respectively. Slide displays 74 indicating the set values of the displayed test image are displayed on the bar displays 71 to 73, respectively.

The user can change the positions of the slide displays 67 and 74 through a predetermined input apparatus to change the respective set values. The user operation is received in step S23. When there is setting change operation by the user, the process shifts from step S24 to step S25. The respective parameters are changed according to the user operation, and then the changed parameters are used to play back the test image. When the user performs confirmation operation through the input apparatus not shown without changing the setting, the set values at the time are confirmed (step S26). In step S27, whether profiling is designated is judged. If the profiling is designated, the profile according to the setting at the time is generated as the base profile in step S28. In step S29, the generated base profile is outputted and stored in, for example, a memory medium.

The base profile can be provided to the base profile input section 46 of the recording and color management apparatus 40 to generate the secondary use profile for the device that uses the medical image for a second time. That is, the surgeon can use a computer or the like in this case to create a profile for obtaining the color tone desired by the surgeon. The display apparatuses 19 and 26 of FIG. 2 and the like can also be designated as the devices that use the medical image for a second time, and the generated secondary use profile can be provided to the display apparatuses 19 and 26 along with the medical image to output the medical image in the color desired by the surgeon to the display apparatuses 19 and 26.

Note that the control section 47 can create a plurality of secondary use profiles corresponding to a plurality of devices that use the medical image for a second time, and the recording data generation section 42 can switch the secondary use profile recorded in association with the medical image according to the output destination to output the secondary use profile according to each output device.

In this way, the profile of the device for displaying the medical image in a color desired by the surgeon during, for example, the surgery is inputted as the base profile in the present embodiment, and the conversion information is used to convert the base profile to the secondary use profile for defining the display color of the device that uses the medical image for a second time. The generated secondary use profile is recorded in association with the medical image. When the recorded medical image is used in the device that uses the medical image for a second time, the device reads the secondary use profile associated with the medical image to set the color. As a result, the device that uses the medical image for a second time can also display and print the medical image in the same color as the medical image observed by the surgeon during the surgery. In this way, the medical image can be displayed and printed in the color desired by the user in any device.

(Second Embodiment)

Figure 12:
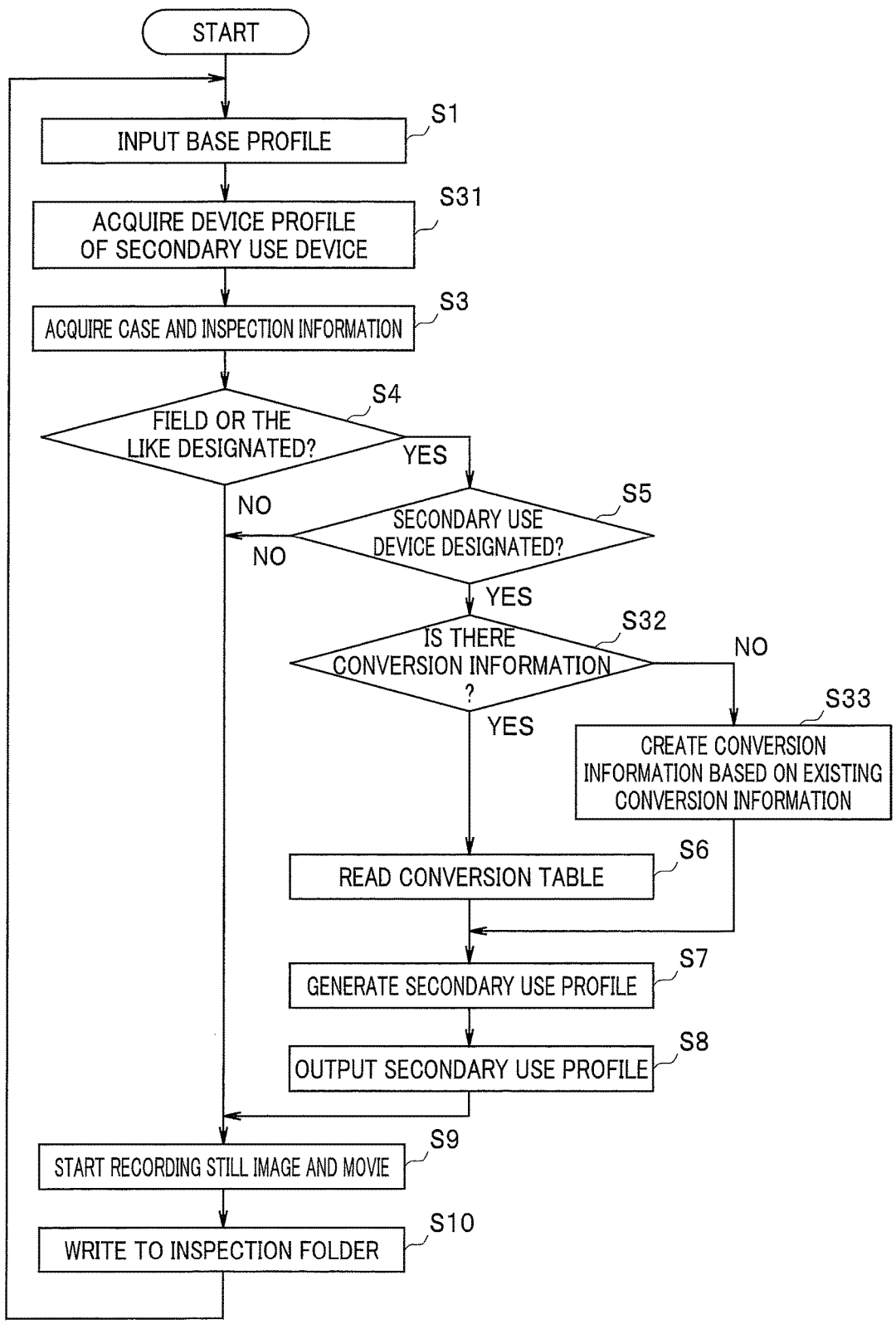
FIG. 12 is a flowchart showing a second embodiment of the present invention.

FIG. 12 is a flowchart showing a second embodiment of the present invention. In FIG. 12, same reference signs are provided to the same procedures as in FIG. 6, and the description will not be repeated. The hardware configuration of the present embodiment is the same as in the first embodiment. FIG. 13 is an explanatory view showing coefficient sequences of conversion information corresponding to scene numbers.

In the example described in the first embodiment, the conversion information corresponding to the device that uses the medical image for a second time is prepared in advance, and the base profile is converted to the secondary use profile corresponding to the device that uses the medical image for a second time based on the conversion information. However, when the conversion information is not prepared for a device designated as the device that uses the medical image for a second time, the secondary use profile cannot be generated in the first embodiment. The present embodiment allows generating the secondary use profile for the device that uses the medical image for a second time even in such a case.

The present embodiment is different from the first embodiment in that a flow of FIG. 12 is adopted in which steps S31 to S33 are added to the flow of FIG. 6. The control section 47 acquires the information of the secondary use device in step S31 of FIG. 12. Note that step S31 includes the process of step S2 of FIG. 6. That is, the information of the registered device is acquired based on, for example, the scene selection of FIG. 7.

The conversion information for a plurality of devices that use the medical image for a second time is also stored in the memory 48 in the present embodiment. Other than the scene number input, the control section 47 allows user input for custom setting in the scene selection of FIG. 7, for example.

Now, it is assumed that conversion information A {X1, X2, ... }, B {X1, X2, ... }, C {X1, X2, ... }, ... shown in FIG. 13 is stored in the memory 48 according to the respective scenes. FIG. 13 shows coefficient sequences of the conversion information corresponding to the scene numbers. For example, if the conversion information related to a scene number No. 2 is as shown in FIG. 5, a coefficient B {X1} is equivalent to {+4, +1, +8}, a coefficient B {X2} is equivalent to {×1.2}, a coefficient B {X3} is equivalent to {−5}, and a coefficient B {X4} is equivalent to {+4}. Note that the respective coefficients with the same number of suffix denote the same setting item related to color.

When a scene number corresponding to the conversion information registered in the memory 48 is designated in the scene selection, the control section 47 acquires the scene number in step S31 and reads the conversion table (conversion information) corresponding to the scene number in step S6. On the other hand, the user performs input operation for custom setting to designate a scene not registered in the memory 48 in the scene selection. In this case, the control section 47 imports the device profile of the device that uses the medical image for a second time through the external device switching section 50. The device profile is color setting information in the device that uses the medical image for a second time. The device profile may be set in advance in the device or may be obtained according to the flow of FIG. 10 or the like. The control section 47 stores the acquired device profile in the memory 48.

The control section 47 judges whether the conversion information related to the secondary use device set by the user is stored in the memory 48 in step S32. When the input operation for the custom setting is performed instead of the scene number corresponding to the conversion information stored in the memory 48, the control section 47 shifts the process from step S32 to step S33 and uses existing conversion information stored in the memory 48 to generate the conversion information related to the secondary use device designated by the user.

Now, it is assumed that the respective coefficients of the device profile imported from the external device switching section 50 are G {Y1, Y2, ... }. Note that when the number of the suffix of the coefficient of the device profile and the number of the suffix of the coefficient of the conversion information are the same, the coefficients denote the same setting item related to color. The control section 47 compares each coefficient G {Y1}, G {Y2}, . . . and each coefficient A {X1} to F {X1}, A {X2} to F {X2}, . . . of the existing conversion information and extracts the closest value. If the extracted value is a value within the range of the respective coefficients of the device profile, the control section 47 sets the extracted value as a conversion coefficient. If the extracted value is a value out of the range of the respective coefficients of the device profile, the control section 47 sets, as a conversion coefficient, a value closest to a value in the range among the values compared for each of the coefficients. In this way, the control section 47 obtains conversion coefficients G {X1, X2, X3 . . . } for obtaining the secondary use profile based on the device profile and the existing conversion information.

The other actions are the same as in the first embodiment.

In this way, the same advantageous effects as in the first embodiment can be obtained in the present embodiment. Even if the conversion information is not prepared for a device designated as the device that uses the medical image for a second time, the existing conversion information can be used to generate the conversion information to obtain the secondary use profile.

The present invention is not limited to each of the embodiments, and in an execution phase, the constituent elements can be modified without departing from the concept of the present invention to embody the present invention. A plurality of constituent elements disclosed in each of the embodiments can be appropriately combined to form various inventions. For example, some of the constituent elements illustrated in the embodiments may be deleted. In addition, constituent elements across different embodiments may also be appropriately combined.

What is claimed is:

1. A color integration system for medical images comprising:
   a first profile setting section configured to set a first profile that is setting information for color reproduction in a plurality of first output environments for outputting a medical image;
   a second profile setting section configured to set a second profile for color reproduction in a plurality of second output environments for using the medical image for a second time;
   a storage section configured to store a plurality of pieces of conversion information for conversion to the second profile set by the second profile setting section based on a setting result of the first profile setting section;
   a control section configured to use the conversion information stored in the storage section to convert the first profile to the second profile; and
   a data generation section configured to output the second profile in association with the medical image,
   wherein if conversion information corresponding to an output environment for using the medical image for a second time is not stored in the storage section, the control section acquires a profile for color reproduction in the output environment, generates conversion information for converting the first profile to the second profile based on the acquired profile and one or more pieces among the plurality of pieces of conversion information stored in the storage section, and uses the generated conversion information to convert the first profile to the second profile.

2. The color integration system for medical images according to claim 1, wherein
   the first profile includes setting information adjusted by a surgeon for the color reproduction of the medical image in at least one of the plurality of first output environments.

3. The color integration system for medical images according to claim 1, further comprising
   a recording section configured to record output of the data generation section.

4. The color integration system for medical images according to claim 1, further comprising
   a profile storage section configured to store a plurality of first profiles corresponding to the plurality of first output environments,
   wherein the control section selects and converts one of the plurality of first profiles to the second profile based on an operation of specifying at least one of the plurality of first output environments.

5. The color integration system for medical images according to claim 4, wherein
   the operation of specifying at least one of the plurality of first output environments is an operation of specifying a medical case or a medical field.

6. The color integration system for medical images according to claim 1, wherein
   the control section selects one of the pieces of conversion information based on an operation of specifying one of the plurality of second output environments to convert the first profile to the second profile.

7. The color integration system for medical images according to claim 6, wherein
the operation of specifying one of the plurality of second output environments is an operation of specifying a system that uses the medical image for a second time.

8. The color integration system for medical images according to claim 1, further comprising in the second output environments:
   a second output environment recording section configured to record the medical image including the second profile;
   a second output environment display section configured to use the second profile to display the medical image;
   a second output environment color adjustment section configured to adjust a color of the medical image displayed on the second output environment display section; and
   a second output environment profile generation section configured to generate a profile corresponding to the color adjustment by the second output environment color adjustment section.

9. The color integration system for medical images according to claim 1, further comprising in the first output environments:
   a first output environment display section configured to display the medical image;
   a first output environment color adjustment section configured to adjust a color of the medical image displayed on the first output environment display section; and
   a first output environment profile generation section configured to generate a profile corresponding to the color adjustment by the first output environment color adjustment section.

* * * * *